(12) United States Patent  
Egorov et al.

(10) Patent No.: US 8,016,777 B1  
(45) Date of Patent: Sep. 13, 2011

(54) HAND-HELD PROBE FOR PROSTATE CANCER SCREENING

(75) Inventors: Vladimir Egorov, Princeton, NJ (US); Armen P. Sarvazyan, Lambertville, NJ (US)

(73) Assignee: Artann Laboratories Inc., Trenton, NJ (US)

( * ) Notice: Subject to any disclaimer, the term of this patent is extended or adjusted under 35 U.S.C. 154(b) by 0 days.

(21) Appl. No.: 12/903,561

(22) Filed: Oct. 13, 2010

(51) Int. Cl.
*A61B 5/117* (2006.01)
*A61B 5/103* (2006.01)

(52) U.S. Cl. ........................................ 600/587

(58) Field of Classification Search .................. 600/587, 600/407
See application file for complete search history.

(56) References Cited

U.S. PATENT DOCUMENTS

| | | | |
|---|---|---|---|
| 6,091,981 A * | 7/2000 | Cundari et al. | 600/407 |
| 2004/0068203 A1* | 4/2004 | Gellman et al. | 600/587 |
| 2007/0293792 A1* | 12/2007 | Sliwa et al. | 600/587 |
| 2010/0087756 A1* | 4/2010 | Egorov et al. | 600/587 |

* cited by examiner

*Primary Examiner* — Brian Szmal
(74) *Attorney, Agent, or Firm* — Boris Leschinsky (57) ABSTRACT

A hand-held probe is configured for a prostate cancer screening test and includes a pressure sensor array, a test progression indicator, a display, and an electronic circuit for processing pressure data. The test progression indicator is configured to guide the operator during the test as to the proper position of the probe about the prostate and the progress of collecting and accumulating test data. Data quality thresholds are used to accept or reject readings from the pressure sensor array. The results are presented as either a high or low probability of prostate cancer. The probe is adapted for easy use in an office of a general practitioner.

9 Claims, 8 Drawing Sheets

FIG. 8

HAND-HELD PROBE FOR PROSTATE CANCER SCREENING

BACKGROUND

Current methods of prostate assessment and prostate cancer detection include Digital Rectal Examination (DRE), Prostate Specific Antigen (PSA) blood test, TransRectal Ultrasound (TRUS), computerized axial scanning tomography (CT) and endorectal Magnetic Resonance Imaging (MRI). Both CT and MRI are not widely accepted by urologists because of complexity of examination and costs associated with these tests. TRUS itself cannot distinguish reliably between cancerous and noncancerous tissue. The most commonly employed screening techniques remain DRE and PSA. During DRE, a health professional inserts a lubricated, gloved finger of one hand into the rectum to check for abnormalities of the prostate by tactile testing of its local and global hardness (elasticity). Normal prostate tissue has the elasticity modulus that is lower than the modulus of prostate cancers. Cancerous tumors have distinguishing elastic properties due to blocking from its blood nutrients as well as certain morphological and physiological modifications.

Screening for prostate cancer remains a controversial issue due to many apparent limitations in both DRE and PSA methods. Although DRE is considered the most cost-efficient method of diagnosis of prostate conditions, its effectiveness is limited by the fact that the test is highly subjective as results depend on examiners training and experience. A need therefore exists for a new device that mimics DRE, but provides objective data on prostate mechanical properties, has enhanced sensitivity and specificity, does not require special skills and years of training, and might consequently provide a more efficient screening yield. Such a device for capturing tactile data from the prostate and assessing its mechanical and geometrical properties without subjectivity of DRE and with sensitivity exceeding that of manual palpation is a subject of this invention. DRE is subjective in its nature since it relies on the abilities of examiner to interpret tactile sensations into a diagnosis. While the method of this invention closely mimics the manipulation part of DRE, it eliminates the necessity to subjectively interpret the tactile sensations.

SUMMARY OF THE INVENTION

It is an object of the invention to provide an electronic palpation device mimicking DRE for prostate cancer screening test, the device is capable of immediately classifying the examined prostate as normal (low probability of prostate cancer) or suspicious (high probability of prostate cancer) and displaying in real time the test result.

It is another object of the invention to provide a probe equipped with a test progression indicator configured to provide guidance to the operator as to the progress and quality of data accumulation during the test.

It is another object of the invention to minimize subjectivity of palpation diagnostics and eliminate dependence on the experience of clinicians. Digital rectal examination may seem awkward to an inexperienced clinician creating a psychological barrier that might decrease the test accuracy.

It is a further yet object of the invention to simplify the training required for conducting prostate cancer screening test. The trainee may have to learn only a few simple steps in the manipulating the probe rather than learning how to relate his tactile sensations to the variety of possible prostate conditions, as it is done during manual DRE.

It is still another object of the invention to simplify the device enough so as to facilitate its use in the office of a general medical practitioner. The hand-held, easy-to-use low cost device with minimum training requirements can be used for prostate cancer screening examination instead of DRE or as an addition to DRE.

The transrectal probe of the invention is equipped with a pressure sensor array which is shaped and configured to fit into a rectum and acquire stress patterns of the prostate gland and surrounding tissues. Readings from the sensor array are continuously analyzed by the device and decisions are made as to whether the readings are likely to be that of a prostate or not. A test progression indicator is provided and configured to inform the operator whether the probe is positioned over the prostate properly and the data accumulated by pressing the probe against the prostate is of acceptable quality for further processing. Is the data is accepted by the device, a degree of completion information may also be communicated to the operator. Acceptance of the data is decided upon by the device using at least one of several data quality thresholds.

Once enough data are accumulated and accepted by the device, stress patterns may be extracted from the data. At least two prostate features may then be calculated from the stress patterns. A data analyzer may then be configured to calculate the probability of the presence of prostate cancer using these at least two prostate features. Finally, the test result is provided to the operator and may include either a category of high probability of prostate cancer necessitating a more detailed follow-up or a category of low probability of prostate cancer.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF THE INVENTION

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

The device for prostate cancer screening is a transrectal probe equipped with a pressure sensor array to obtain at least one or preferably multiple stress patterns of prostate and surrounding tissues as a result of transrectal compressions of tissue in vicinity of a prostate. The probe includes an electronic circuit configured for acquisition of a tissue stress pattern and a signal processor for real time computing using the stress pattern of at least two prostate features, the features may be selected from a group consisting of elasticity contrast, heterogeneity, prostate shape, prostate mobility and prostate deformability. The probe includes a test progression indicator designed to indicate in real time the amount of data that is already accumulated and accepted by the device as having adequate quality for further processing. The test progression indicator is useful in guiding the operator during the test. Once sufficient data is accumulated, the probe is configured to immediately determine the test outcome based on the calculated prostate features. Test result may be categorized as either a category of a high probability of prostate cancer or a category of a low probability of prostate cancer. Inadequate data collection may result in a third test outcome, namely a message of inadequate quality of stress patterns. The probe may further include a display for communicating the test results to the clinician.

Figure 1:
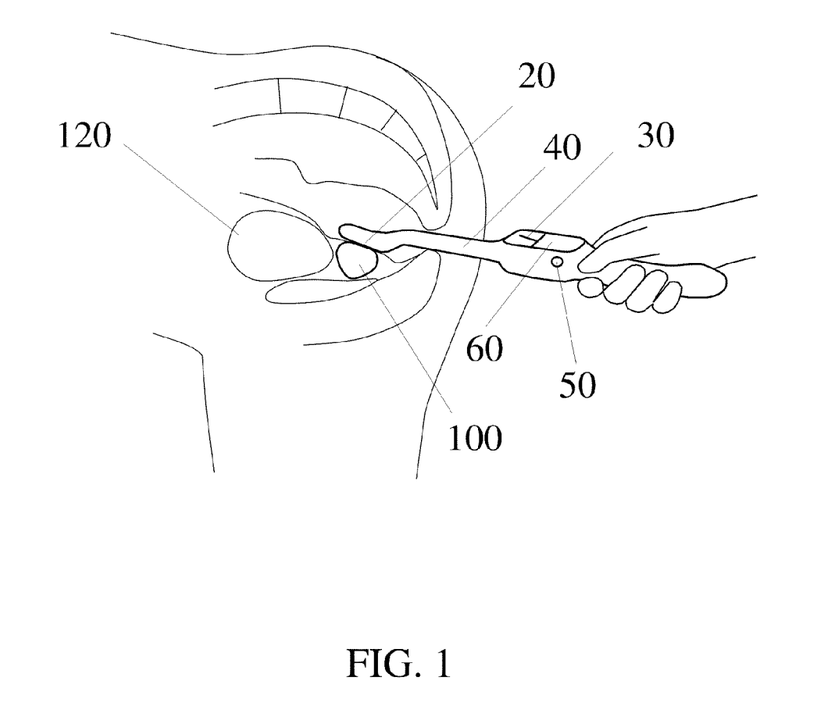
FIG. 1 is a general diagram illustrating the screening test procedure using the device of the invention.
Figure 2:
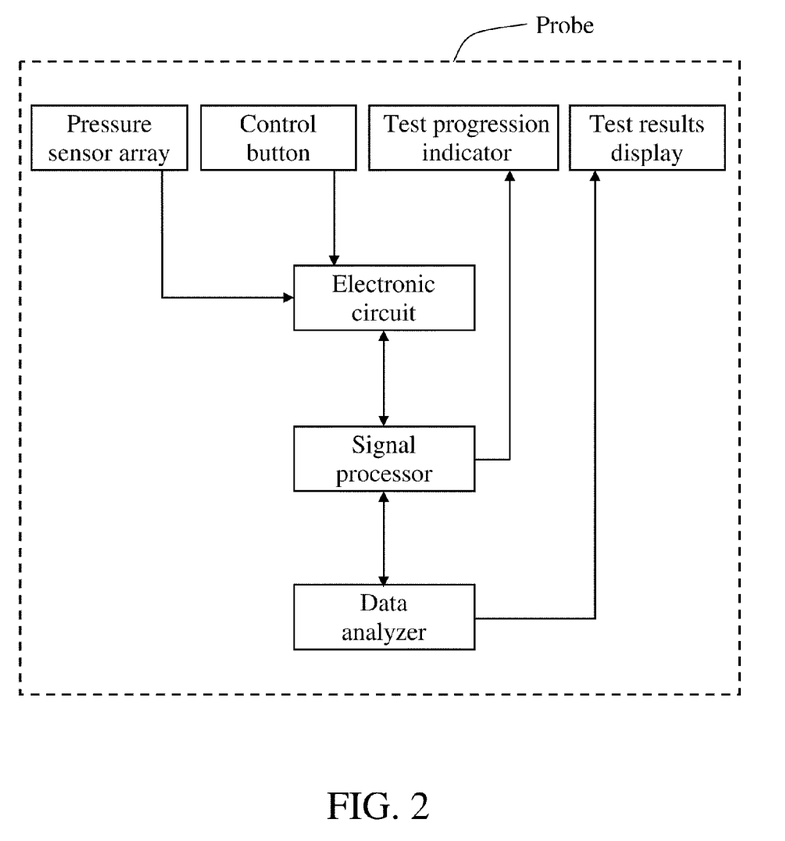
FIG. 2 is a general block-diagram of one embodiment of the invention showing a self-contained device of the invention.

FIG. 1 shows a device for prostate cancer screening and FIG. 2 presents a general block-diagram of the device. The device includes the following key elements:

a transrectal probe 40 equipped with a pressure sensor array 20 to obtain tissue stress patterns over the prostate 100 resulting from prostate compressions using the probe, a multifunctional button 50 to control the device operation, a test progression indicator 30, an electronic circuit for signal acquisition from the pressure sensor array, a signal processor for real time data processing and extracting from the stress patterns at least two or more prostate features; the features may be selected from a group consisting of elasticity contrast, heterogeneity, prostate shape, prostate mobility and prostate deformability, a data analyzer for categorizing the test outcome using the extracted prostate features as a high or a low probability of prostate cancer, or in some case as inadequate quality of stress patterns; and a display 60 for displaying the test results.

Figure 3:
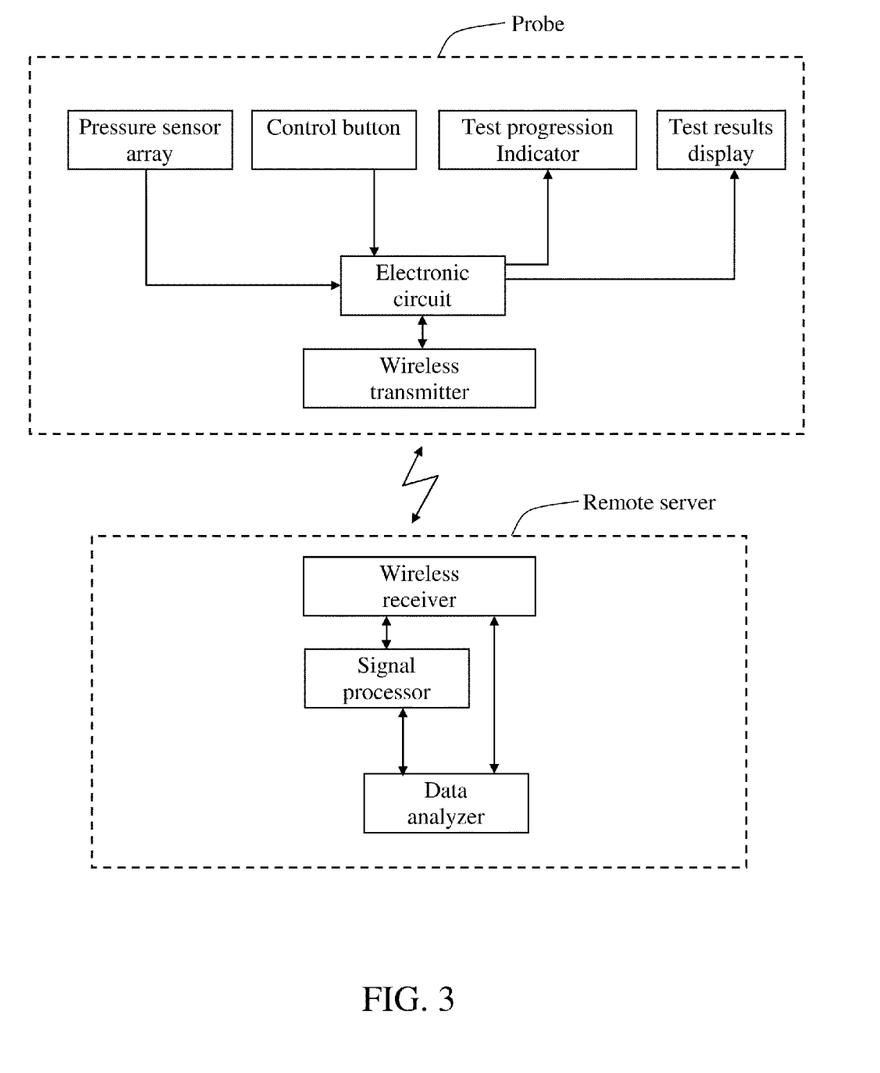
FIG. 3 is a general block-diagram of another embodiment of the invention showing a probe equipped for communicating with a remote server.
Figure 4:
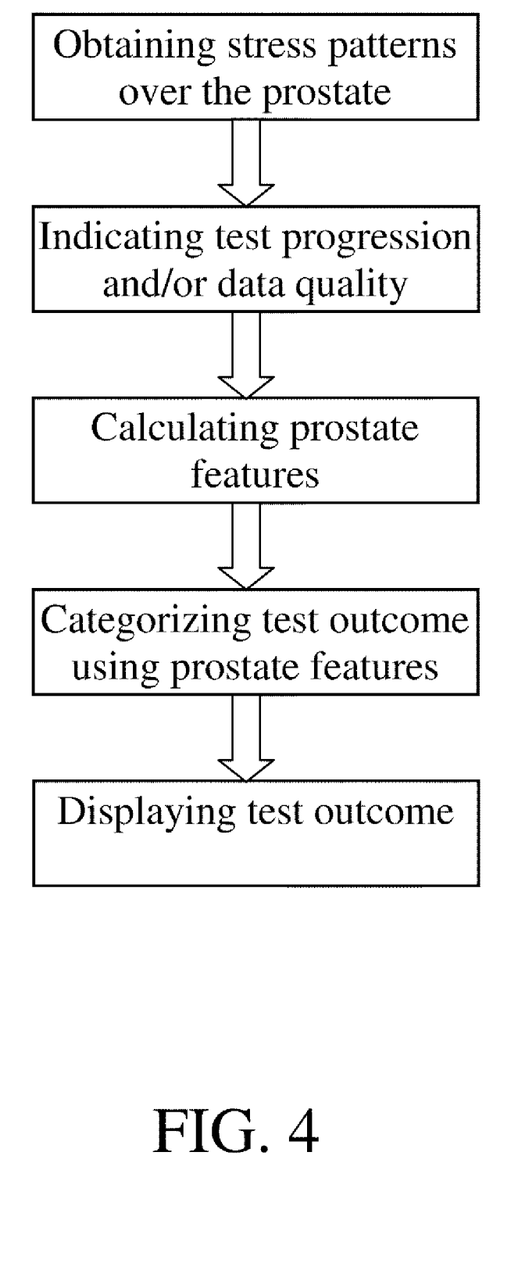
FIG. 4 is a block-diagram showing the procedure sequence of the screening test.

The electronic circuit, the signal processor, the data analyzer and the display may be incorporated into the probe handle to make a self-contained device. The device may further comprise a wired communication using a cable or a wireless communication using a transmitter for data exchange with external network such as a remote server to facilitate remote data processing as shown in FIG. 3. In embodiments, the signal processor and the data analyzer may be moved to the remote server. The term "remote server" is used herein to include network servers as well as any other external electronic devices that may be adapted to communicate with the transrectal probe and process information obtained from the probe. The network server may provide the device software update, hardware troubleshooting and operator training. One example of such external electronic device is a mobile phone. In embodiments, a wireless data transmission may be established between the transrectal probe of the invention and a mobile phone using one or available data transmission protocols such as, for example, a Bluetooth. In its basic form, data is transmitted to the mobile phone to be further sent to another server for processing and/or data recording. In other embodiments, data is received by the mobile phone for processing internally and even in some cases for communicating back to the probe of the invention for displaying the results. In a sense, an external smart phone may be used to fulfill at least one or more of the data processing or even visualization and control functions for the transrectal probe.

The transrectal probe is shaped to fit inside a rectum. The pressure sensor array may be installed on the probe head surface and configured for contacting with prostate through the rectal wall during the examination procedure. The probe may include a tilt sensor to provide probe rotational angle around the probe longitudinal axis passing through the probe handle and probe head (tip). A thin elastic disposable sheath may be used to cover the probe. The sheath may be selected to have mechanical properties which do not influence the stress pattern measured by the probe. The sheath may be used to protect the surface of the probe head and the probe shaft. The test progression indicator may be an audible or preferably a visual indicator. In the most basic embodiment of the invention, the test progression indicator switches from a state indicating incomplete data to a state indicating the presence of sufficient data once adequate amount of acceptable data is collected. In a more advanced embodiment of the invention, the test progression indicator is configured to continuously communicate the amount of data accepted by the device to the operator so as to provide information about the progress of data collection. This can be done in a variety of ways, for example as a percentage display (numeric, bar chart, pie chart, etc); as a blinking light with variable frequency of blinking (faster blinking showing more data); as a light changing color from a first color indicating no data to a second color indicating completion of data collection; or as a series of lights configured to turn on more lights as more data is collected. The test progression indicator may be configured to indicate the absence of acceptable data prompting the operator to adjust the testing technique.

The test progression indicator of the invention may be configured for spatial guidance so that the operator is aware of the proper or improper position of the probe over the prostate. In embodiments, the probe may include a library of expected prostate stress patterns so the real time stress pattern which is read from the pressure sensor array may be recognized as that of a prostate or not—a result of that recognition may be communicated to the operator.

In other embodiments, the probe may be configured to expect a particular bell-shaped stress pattern when the probe is pressed against the prostate. As the prostate tissue is normally more firm than the surrounding tissues, a characteristic bell-shaped stress pattern is formed when the probe is properly positioned.

An optional indicator of the center of prostate may be displayed for the operator so as to guide the movements of the probe. The displayed center or a top of the prostate may correspond to the recognized center of the bell-shaped stress pattern that is selected to represent a prostate. This allows using the test progression indicator for proper positioning of the probe over the prostate during examination. In embodiments, the test progression indicator may be configured to not advance to the next stage if the probe of the invention is not positioned properly.

The electronic circuit of the probe may be configured for data acquisition process which starts after initialization and includes constant or intermittent scanning of all sensors of the pressure sensor array. The electronic circuit may be further configured for digitizing received analog signals; buffering the data stream and dividing it into frames (a set of records from all sensor signals; and forwarding the signal to processing and visualization. The signal processor may be configured for primary data filtering and optionally for visualization of the current data frame as an image on the display. The basic mode of visualization may include only the test progression indicator without any images as the clinician is instructed to manipulate the probe using visual guidance and the test progression indicator. The signal processor is further configured to extract various prostate features and includes a data analyzer to determine the outcome of the test as described in more detail below.

Examination may begin with initialization of the device by pressing the control button 50. After initialization, the device may be ready for use, and may automatically detect stress patterns resulting from tissue compression. The test progression indicator is also activated. The probe may then be placed in a rectum (see FIG. 1) and the test procedure may be initiated while the acquired data may be recorded as a file.

Typically, the examination may take no more than 15-30 seconds. The examination may be performed by asking the patient to bend over the examination table to form a 90-degree angle at the waist or lying down on the table on a back as during TRUS guided biopsy. In the first position the patient' chest may be placed on the table and the patient's weight is applied to the table surface so that leg muscles are free from any tension. The probe may be covered with a disposable lubricated sheath. Gentle posterior pressure may be applied as the probe is slowly inserted with the probe head sensor surface facing down. Scanning begins after the pressure sensor is moved past the sphincter. Then, the probe may be inserted deeper and the prostate may be detected at about 4-5 cm from the sphincter but prior to reaching the bladder 120. The examination may consist of at least one or preferably multiple compressions of the median groove and lateral lobes of the prostate and surrounding tissues by the probe of the invention. Examination technique may include multiple sliding the probe tip over the prostate from left to right and vice verse while pressing onto the prostate. The optional average pressure reading may be provided to advise the operator that the probe is applied with a pressure within or exceeding a predefined comfort pressure limit for the patient. A further optional visual or audible indicator may be used to confirm sufficiency of the pressure applied during the compressions for the purposes of data acquisition—an alarm may be activated should the pressure be insufficient for data analysis.

Two software components may support device functionality: an electronic circuit-embedded software, and a network software on a remote server or a smart phone. The first software component may provide for low-level operations such as pressure sensor multiplexing, signal amplification, sensor sensitivity and offset control, analog-to-digital conversion of acquired signals, data processing, categorizing and indicating on the display as well as data transfer through the Internet or cell phone network to the remote server. The second software component may provide further data processing and analysis. The exact point of division of the software into two components may depend on specific features of proposed embodiments. In other embodiments, the entire software may be resident in the probe itself.

For the purposes of categorizing the test outcome, at least two prostate features may be extracted from collected stress patterns. The elasticity contrast may be extracted as a ratio of a pressure peak within the stress pattern to an average pressure response pattern produced by a prostate tissue surrounding suspected prostate abnormality. The heterogeneity may be extracted as a standard deviation for local singularities in prostate pressure patterns. The prostate mobility may be extracted as a prostate global displacement under compression by the probe. The prostate deformability may be extracted as a prostate capability to change its shape under compression by the probe.

The step of categorizing of test outcome may be implemented with the use of a classifier such as a linear classifier, a decision tree classifier, a statistical classifier, a Bayesian classifier, a neural network classifier, a fuzzy logic classifier, a support vector machine classifier, or a classifier with principal component analysis. A classifier may involve supervised leaning, reinforced leaning, or unsupervised leaning. The classifier accepts the selected prostate features as input values to calculate probability that the prostate cancer is present. The implemented classifier may be adjusted using a clinical data set including all prostate features calculated by the device and known cancer positive/negative outcomes derived from the prostate tissue pathology analysis which is currently used as a gold standard.

The main advantage of the probe of the invention is that it does not require any decision making from an operator. The operator is only asked to follow the prostate examination procedure which requires two probe manipulations: applying load to prostate and moving the probe head to left/right side of the prostate. The data collected during the test is analyzed for sufficiency. If the data does not satisfy predetermined data quality thresholds, the examination will be classified as having inadequate data quality and operator will be asked to repeat the prostate examination.

The data quality thresholds may include requirements for a predetermined applied pressure distribution, a minimum number of frames with the prostate imprints, a minimum number of prostate compressions, a minimum size of palpated zone, and/or an established an acceptable range of rotational angles.

The pressure distribution may be defined for average value of pressures measured on all pressure sensors of the pressure sensor array. In embodiment, the following requirements may be used for the average pressure value:
   (a) the entire operating pressure range (for example between about 8 kPa to about 33 kPa) may be divided into a number of as sub-ranges with a predefined pressure difference width, such as for example 2.5 kPa; each pressure sub-range must include at least 10 data frames;
   (b) a number of frames with 33 kPa may not exceed a certain maximum, such as for example 50;
   (c) a ratio of a number of frames with pressure below 8 kPa to a number of frames with pressure above 8 kPa may not exceed a predefined number such as for example 5.

The minimum number of frames with acceptable prostate imprints when a recognized prostate stress pattern is detected in a pressure pattern acquired by the pressure sensor array may be at least 80. Prostate presence is recognized when a bell-like stress pattern is detected with a maximum inside pressure sensing area excluding about 3 mm from a pressure sensor array perimeter.

The minimum number of acceptable prostate compressions by the probe may be at least 5. Each acceptable compression may be characterized by a phase of the average pressure loading curve, an average pressure maximum, and an average pressure unloading curve. Acceptance criteria may include:
(a) the average pressure loading curve must include at least 5 pressure frames,
(b) the average pressure unloading curve must include at least 5 pressure frames, or
(c) the average pressure maximum must exceed 30 kPa.

In embodiments, all three acceptance criteria may be used at the same time.

The minimum size of palpated zone may be calculated as an area of accepted reading from a pressure sensor array. In embodiments, the minimum palpated zone may be selected to be between about 1 $cm^2$ to about 4 $cm^2$ and preferably 2 $cm^2$. In this case, any readout from the pressure sensor array that is smaller than the selected minimum size of palpated zone is excluded from further calculations.

The acceptable range of rotational angles may be selected to be within ±15 degrees. The rotational angle is defined as a tilt of the probe relative to its longitudinal axis. Rotational angle of 0 degrees corresponds to an orientation of the probe when the pressure sensor array is parallel to the prostate surface. Deviations beyond ±15 degrees in the rotational angle may skew the pressure patterns by adding an edge effect to the reading of the pressure sensor array which may influence the data analysis outcome. The edge effect may result from compression of the tissue by a portion of the probe not equipped with pressure sensors.

Once the data is judged by the device as satisfactory for data analysis, the probe may be configured for automatic categorization of the test outcome into either a category of high probability of prostate cancer (or suspicious prostate conditions) or a category of low probability of prostate cancer (normal prostate conditions). Test results may then be displayed. All operators, if they followed the prescribed prostate examination technique, will have the same result for the same prostate conditions. The method therefore excludes any subjective data interpretation by operator and may not require DRE.

Further increase in operator's confidence may be achieved by training using a computerized setup. The operator skill testing in prostate examination technique may be formalized with the use of the setup including a realistic model of male pelvic anatomy with an elastic rectum and a changeable prostate phantom mimicking various conditions of prostate size, elasticity, and nodularity. An operator performance descriptor may be used to characterize the quality of prostate examination data and the level of practical operator skills in prostate examination by the probe. The operator performance descriptor may integrate all the features used by the device of this invention to characterize the quality of prostate examination.

Alternative embodiments of the invention are now described in more detail and illustrated in FIGS. 5-8.

Human sense of vision provides for fast and comprehensive understanding of data. Visual pattern analysis is the most efficient and comprehensive method of analysis for humans. Visual analysis enables data to be interpreted holistically using the ability of the human eye to comprehend complicated patterns with just a quick glance.

Figure 5:
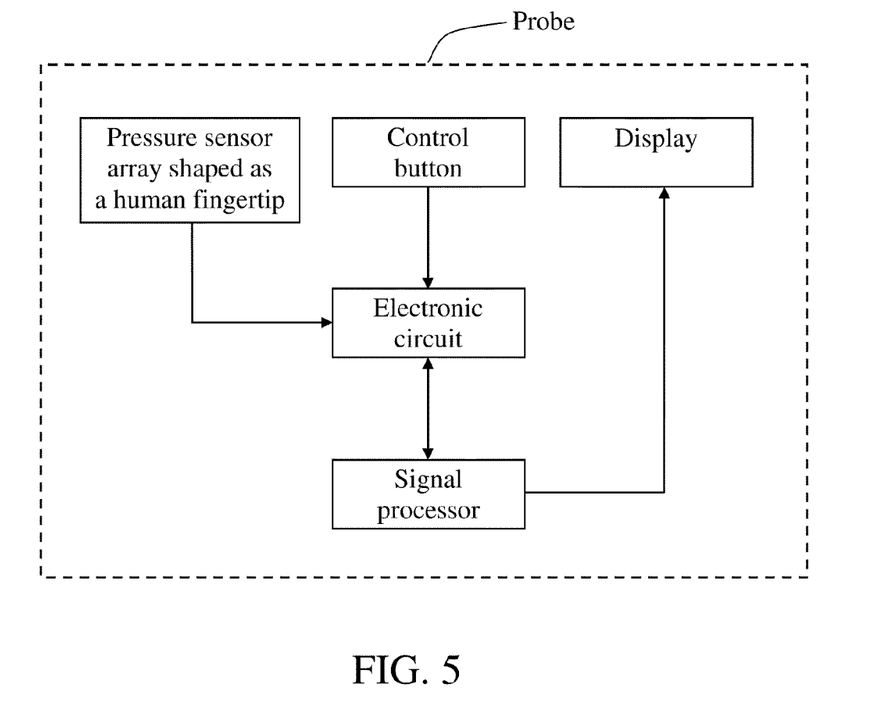
FIG. 5 is a general block-diagram showing yet another embodiment of the invention in which the probe is shaped as a human fingertip.

In embodiments, the probe 40 of the invention is configured to replace human tactile analysis with a visual analysis of a tactile stress pattern 22 recorded using a probe of the invention. The pressure sensor array 20 is shaped as a convex oval to mimic a human fingertip so that a display of a tactile pattern closely resembles the tactile pattern sensed by the human fingertip. In DRE, diagnostic information is obtained as a result of analysis of tactile information transmitted by finger nerves to a human brain. Comprehensive tactile pattern analysis requires long training. Also, human tactile sensory analysis is incomparably inferior to a visual pattern analysis. The latter is by far the most powerful and efficient way in both extracting useful information and developing a conclusion. Thus, displaying probe-obtained tactile patterns for visual analysis by a human operator is aimed to replace traditional human tactile sensory analysis with a visual analysis. This feature may greatly enhance palpation diagnostics accuracy because of the ability of the human eye to understand structure and detect patterns. Visual data may allow the operator to detect prostate abnormalities with just a quick glance.

Figure 7:
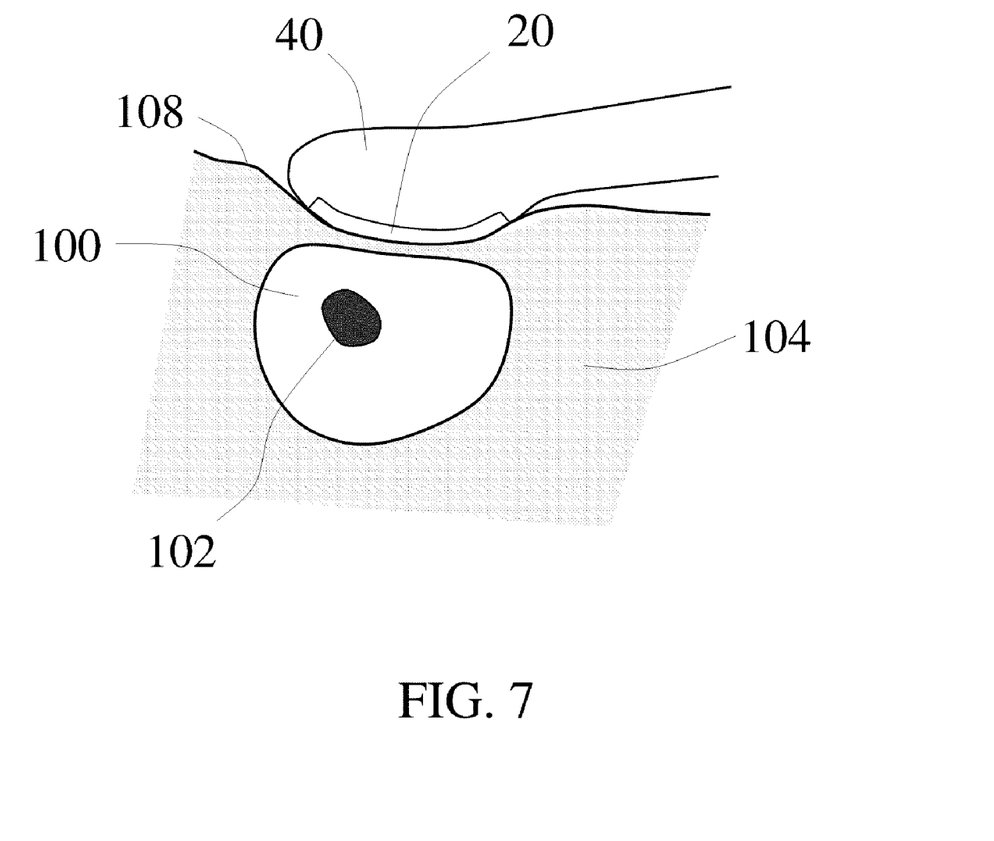
FIG. 7 is an illustration of how the probe shown in FIG. 5 is used to compress prostate and surrounding tissues; and finally
Figure 8:
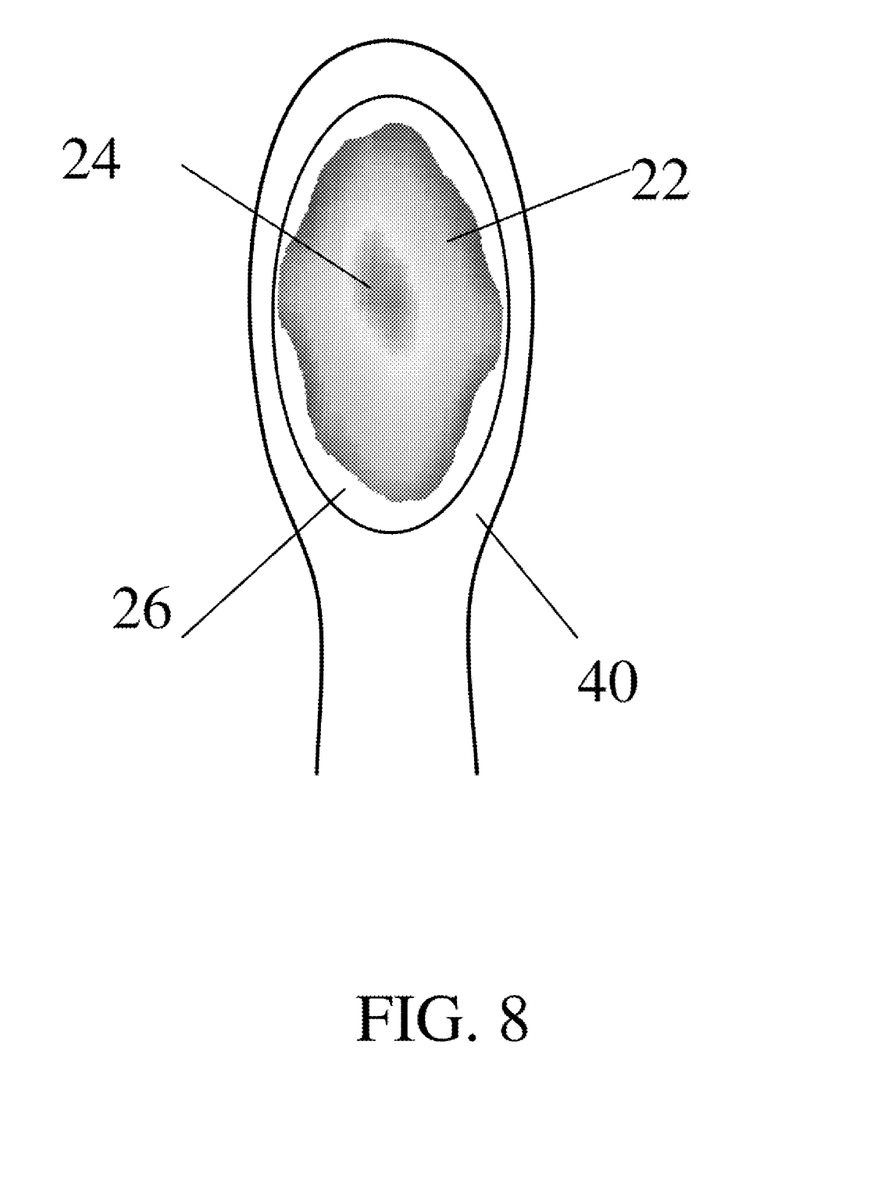
FIG. 8 is an illustration of the oval-shaped stress pattern obtained from the probe shown in FIG. 5.

A method for a prostate cancer screening test for this embodiment of the invention may include the following steps:
(a) obtaining at least one stress pattern of the prostate 100 including a possible lesion 102 resulting from a compression of the prostate 100 and surrounding tissues 104 through the rectal wall 108 using a transrectal probe 40 equipped with a pressure sensor array 20, the pressure sensor array is shaped as a convex oval to resemble a human fingertip;
(b) displaying an oval tactile image 22 of a prostate including a hard lesion 24 (shown in FIG. 8); and
(c) visually analyzing the stress pattern of said tactile image to detect a presence or absence of a prostate abnormality.

This method will help a physician to comprehend and analyze the tactile data better through using visual analysis rather than tactile sensory analysis.

Figure 6:
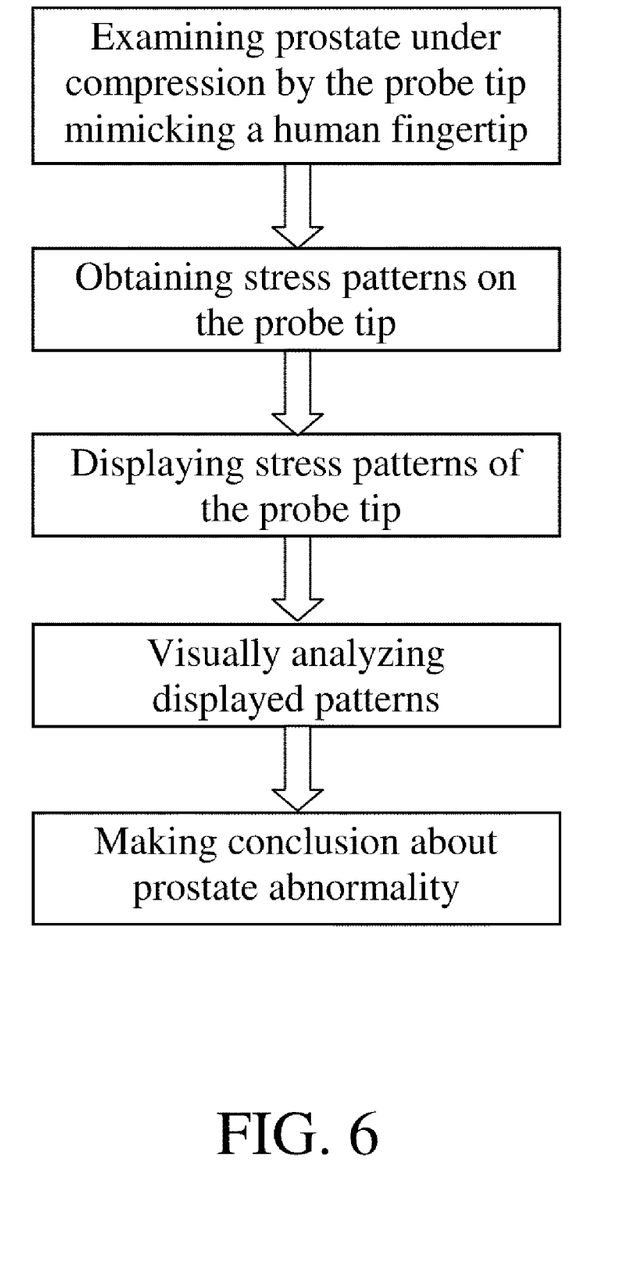
FIG. 6 is a block-diagram showing the procedure sequence of the screening test using a probe shown in FIG. 5.

FIGS. 5-8 show the details of this embodiment of the device for prostate cancer screening. FIG. 5 shows its block diagram and FIGS. 6 and 7 illustrate its use. The device comprises a transrectal probe equipped by with pressure sensor array which is shaped as a convex oval to closely mimic a human fingertip. The probe also includes a multifunctional button to control the device in operation, an electronic circuit for signal acquisition from the pressure sensor array, a signal processor for real time data processing; and a display coupled to the probe for displaying the current stress pattern recorded by the pressure sensor array. The electronic circuit, the signal processor, and the display may be incorporated into the probe handle.

The probe of the invention offers a new method of teaching trainees by allowing visual analysis of tactile patterns. Despite its inherent subjectivity and consequent disagreement in results, DRE is an indispensable tool in an arsenal for the prostate assessment. It is widely used to diagnose benign and cancer tumors and tissue growth in this organ. This diagnostic procedure is a part of virtually every genitourinary examination in older men, and it is endorsed by various cancer societies for the screening of the prostate cancer.

The probe of the invention will allow experienced physicians to easier and better explain to trainees how the tactile pattern peculiarities are related to different conditions of the prostate. Currently, DRE training is achieved via an autodidactic process without much mentorship and feedback. Having tactile data in the visual form will allow an experienced physician to teach trainees more efficiently by showing the tactile pattern as opposed to just describing it. The probe will further improve the ability of trainees to better understand their own sensations during DRE.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A hand-held device for a prostate cancer screening test, the device comprising:
    a transrectal probe equipped with a pressure sensor array configured to obtain at least one stress pattern of the prostate resulting from prostate compressions using said probe,
    a test progression indicator configured to provide feedback indicating sufficient data is acquired by the device to allow for an automatic categorizing of a test outcome,
    a signal processor configured to extract from said stress pattern at least two prostate features, said prostate features selected from a group consisting of elasticity contrast, heterogeneity, prostate shape, prostate mobility and prostate deformability,
    a data analyzer using the extracted prostate features as inputs, said data analyzer configured for said categorizing of said test outcome of said screening test as either a category of high probability of prostate cancer or a category of low probability of prostate cancer; and
    a test result display for communicating the test outcome.

2. The hand-held device as in claim 1, wherein said test progression indicator is further configured to indicate progress of accumulating acceptable test data.

3. The hand-held device as in claim 1, wherein said test progression indicator is further configured to indicate absence or insufficiency of acceptable test data.

4. The hand-held device as in claim 1, wherein said test progression indicator is configured to indicate proper position of said transrectal probe over the prostate.

5. The hand-held device as in claim 4, wherein said test progression indicator is configured for spatial positioning the probe relative to the center of prostate.

6. The hand-held device as in claim 1, wherein said signal processor is further configured to reject or accept readings from said pressure sensor array using a data quality threshold.

7. The hand-held probe as in claim 6, wherein said data quality threshold is selected from a group consisting of a predetermined applied pressure distribution, a minimum number of frames with the prostate imprints, a minimum number of prostate compressions, a minimum size of palpated zone, and an acceptable range of rotational angles.

8. The hand-held probe as in claim 1 further configured for wired or wireless communication with a remote server.

9. The hand-held probe as in claim 1 further configured for communication with a mobile phone.

* * * * *